United States Patent [19]

Radici et al.

[11] 4,088,818

[45] May 9, 1978

[54] PROCESS FOR THE RECOVERY OF FORMALDEHYDE PRESENT IN WASTE WATERS

[75] Inventors: Pierino Radici, Turate (Como); Pietro Erini, Olgiate Olona (Varese); Umberto Santini, Legnano (Milan); Paolo Colombo, Saronno (Varese), all of Italy

[73] Assignee: Societa Italiana Resine S.I.R. S.p.A., Milan, Italy

[21] Appl. No.: 692,408

[22] Filed: Jun. 3, 1976

[30] Foreign Application Priority Data

Jun. 11, 1975 Italy .............................. 24240 A/75

[51] Int. Cl.$^2$ .......................................... C07D 295/02
[52] U.S. Cl. ................................................... 544/186
[58] Field of Search ......................... 260/248.6, 248.5; 544/185, 186

[56] References Cited

U.S. PATENT DOCUMENTS 3,538,199  11/1970  Weiss et al. ...................... 260/248.6
3,843,643  10/1974  Ackerman et al. ............... 260/248.5

FOREIGN PATENT DOCUMENTS 510,236  2/1955  Canada .............................. 260/248.6
252,609  6/1926  United Kingdom .............. 260/248.6

OTHER PUBLICATIONS

Meissner et al., *Industrial & Engineering Chemistry*, vol. 46, pp. 724–727, (1954).

*Primary Examiner*—John M. Ford
*Attorney, Agent, or Firm*—Sughrue, Rothwell, Mion, Zinn and Macpeak

[57] ABSTRACT

Formaldehyde present in a waste water containing lower carboxylic acids is recovered by reacting said waste water at 0° to 90° C with the amount of ammonia required for converting said formaldehyde into hexamine and the latter is recovered in solid form by evaporating the resulting solution.

The solid hexamine thus recovered has a content in lower carboxylic acids not exceeding 0.05 wt.%, is practically free from other impurities and is suited for any conventional use.

15 Claims, 1 Drawing Figure

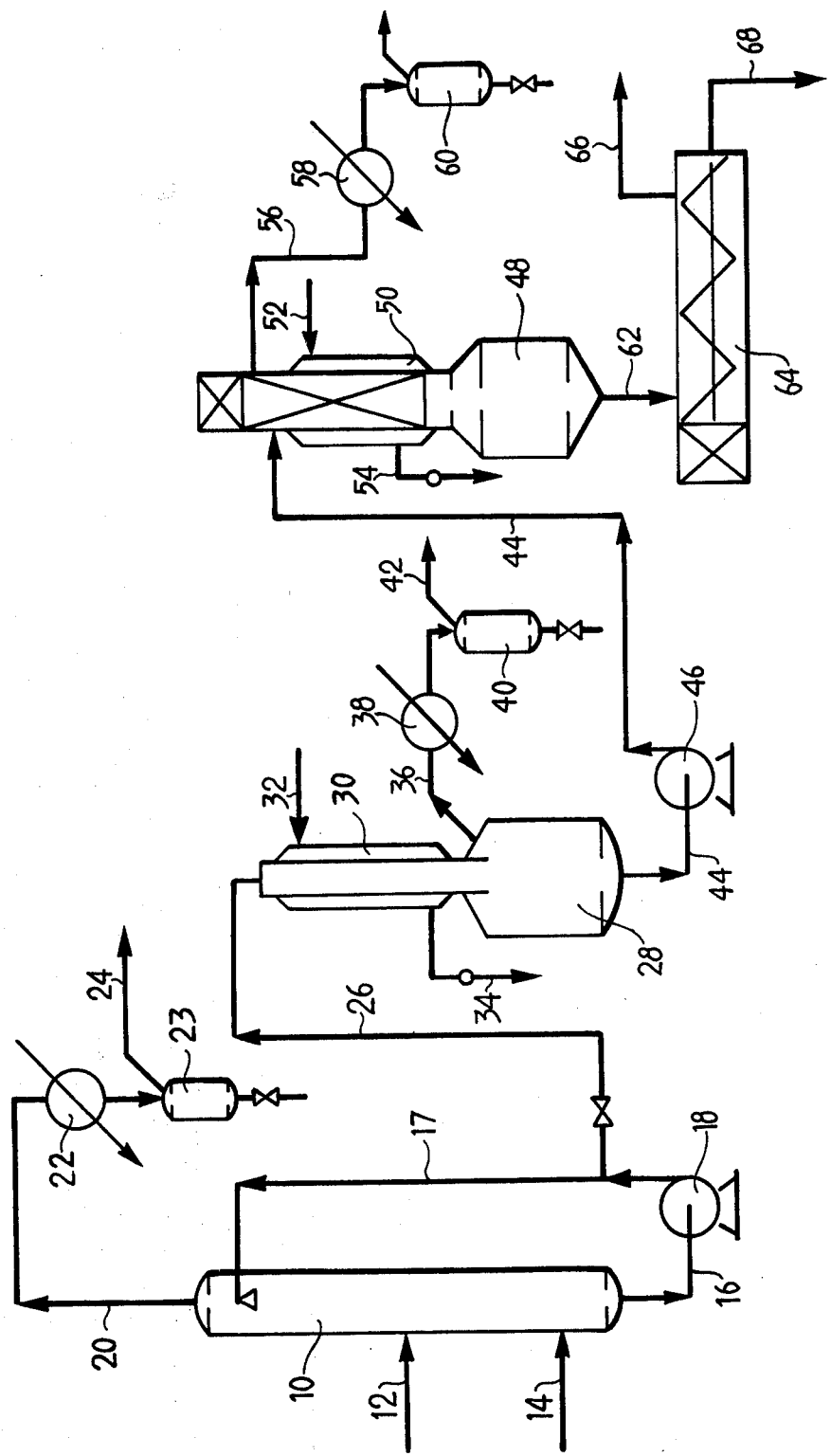

PROCESS FOR THE RECOVERY OF FORMALDEHYDE PRESENT IN WASTE WATERS

The present invention relates to the recovery of formaldehyde from industrial waste waters.

More particularly, the invention relates to a process for the recovery in the form of useful product, of the formaldehyde present in waste waters containing lower saturated carboxylic acids (such as formic, acetic and propionic acids) and possibly other polluting substances such as methanol, methyl formate, methylal or other derivatives of formaldehyde.

Aqueous solutions of the this type derive from commercial processes for the production of acetal polymers, or else from the preparation processes of paraformaldehyde, especially from the concentration step of the aqueous solutions of formaldehyde. The practically complete removal and the recovery of the impurities contained in these waste waters are important both for the productivity of commercial production lines and for anti-pollution reasons. It also stands to reason that the economic aspect of such a treatment is of importance, especially in view of the considerable amounts of wastes involved and the low concentrations of the polluting products present in these wastes. These polluting products can be removed by chemical or physical methods. Thus, for example, the acids may be removed by means of anionic exchange resins and the residual aqueous solution then concentrated.

This procedure is not free from drawbacks, since the active groups of the exchange resins, generally consisting of quaternary ammonium groups, may give rise to side reactions with formaldehyde, for example the Cannizzaro's reaction which leads to the formation of methanol and formic acid. Therefore, it is necessary to use weakly basic anionic exchange resins. The holding capacity of the latter is however rather limited and this fact bears heavily on the operation costs. Moreover, the removal of the solution from the resin and the washing of the latter require large amounts of water, with consequent dilution of the wastes under treatment. Another drawback resides in the important cost of the regeneration of the exhausted exchange resins.

The drawbacks of the prior art are overcome according to the present invention by means of a simple and economical process which allows the complete removal of formaldehyde and its recovery in the form of a useful product, from the waste waters containing lower saturated carboxylic acids and possibly other impurities, such as methanol, methyl formate, methylal and other derivatives of formaldehyde.

Thus, the invention provides a process for the recovery of formaldehyde from a waste water containing the latter together with one or more lower saturated carboxylic acids, characterized by reacting at a temperature of from 0° to 90° C said waste water with an amount of ammonia substantially equal to that required for converting the formaldehyde present in said waste water into hexamine (hexamethylene-tetramine), thereby to obtain an aqueous solution containing hexamine and said carboxylic acids, and evaporating said aqueous solution at a temperature of from 20° to 120° C during a period of from 2 hours to 3 seconds, thereby to recover said hexamine in solid form.

The present invention will now more fully described, by way of example only, with reference to the accompanying drawing, which illustrates an apparatus for carrying out an embodiment of the invention.

The present invention is essentially based on the fact that ammonia introduced into the above waste water in an amount substantially equal to that stochiometrically required for producing hexamine, reacts with formaldehyde instead of salifying the carboxylic acids present in the waste water.

Therefore, the acids can be distilled off together with water in the subsequent evaporation step, this making it possible to produce hexamine with an acid content not exceeding about 0.05% by weight. The other possible impurities previously alluded to, are also removed by evaporation.

Moreover, a low evaporation temperature and/or a short evaporation time should be maintained for producing hexamine free from coloured by-products of unpleasant smell.

The waste waters which are treated according to the process of the present invention may have a formaldehyde content as low as 1% by weight, whereas the upper concentration limit is not critical.

Usually, the formaldehyde content is of from 5 to 25% by weight, whereas the content in lower saturated carboxylic acids (formic, acetic and propionic acids) and possible formaldehyde derivatives is from 0.3 to 20% by weight.

According to the process of the present invention, ammonia is introduced into the waste water up to the amount stochiometrically necessary to convert formaldehyde into hexamine, or at least very close to this value. It is preferred to use gaseous ammonia for the purpose of avoiding any dilution of the waste water.

Operation is preferably carried out at a temperature of from 10° to 60° C and at a pressure equal to or lower than atmospheric.

Under these conditions, the conversion of formaldehyde into hexamine is very speedy, even when a waste water having a very low formaldehyde content is treated.

There has been noted no impediment to the formation of hexamine by the aliphatic carboxylic acids or the other impurities present.

Moreover, the selectivity of the reaction is such as to allow the almost complete conversion of the formaldehyde present in the waste water.

The reaction between ammonia and formaldehyde is strongly exothermic (81 Kcal/mole) and thus, according to a preferred embodiment, the heat evolved is used for evaporating the impurities having a low boiling point, such as for example methylal, methanol and methyl formate, in addition to a part of the water.

In this case, it is convenient to maintain a subatmospheric pressure or to pass air or an other inert gas through the reacting mass.

The impurities thus removed may be condensed and recovered, or else may be burnt, according to economic considerations.

According to the present invention, the aqueous hexamine solution is evaporated and during this operation there are maintained low temperatures and/or short residence times.

More particularly, the evaporation temperature is chosen in the range of from 20° to 120° C, the correpsonding pressure being generally maintained, at atmospheric or subatmospheric value.

The evaporation time is chosen in the range of from 3 seconds to 2 hours, taking into account that the higher the evaporation time, the lower should be the evaporation temperature.

The best results are obtained by carrying out the evaporation at a pressure equal to or lower than atmospheric, at a temperature of from 40° to 100° C and for a period of from 3 seconds to 1 minute.

The evaporation is preferably carried out by a twostep technique. More particularly, in the first step the solution is concentrated to obtain a hexamine content higher than 25% by weight, preferably higher than 35% by weight and not exceeding the saturation value, whereas in the second step solid hexamine is obtained with a water content lower than 1% by weight.

In the two-step evaporation the overall evaporation time and the temperature are maintained within the above indicated ranges of values.

During the evaporation, the less volatile impurities and those which do not give rise to the formation of azeotropic mixtures are also removed from the solution. In particular, there are removed the lower carboxylic acids present such as formic, acetic and proprionic acids.

When short evaporation times are used, devices suitable for the purpose are chosen, such as static or dynamic evaporators of the thin or falling film type.

In any case, operating according to the process of the invention, not only are the impurities removed, but there is avoided the hexamine degradation which leads to the formation of amine by-products which are coloured and of unpleasant smell.

The hexamine recovered after evaporation typically has a water content lower than 1% by weight, a content in carboxylic acids equal to or lower than 0.05% by weight, whereas the other impurities such as the derivative products of formaldehyde or hexamine are practically absent.

If necessary, this hexamine may be further dried, for example in a conventional powder drier, and in any case the end product is suitable for all the uses known in the art.

In the following Examples, the parts and percentages are intended by weight, unless otherwise specified.

EXAMPLE 1

59.16 parts of gaseous ammonia are gradually added to 1,000 parts of an aqueous solution containing 156.6 parts of formaldehyde and 131 parts of acetic acid, while maintaining the mass under agitation.

Besides, operation is carried out at 10° C, by means of external cooling with brine at −10° C, and at atmospheric pressure. During reaction samples are taken and submitted to analysis.

The results of these analyses are reported in Table 1, wherein the parts of added ammonia are shown under (A), the parts of residual formaldehyde in the solution are indicated under (B), the parts of hexamine formed under (C) and the conversion percentage of ammonia into hexamine under (D).

TABLE 1

| (A) | (B) | (C) | (D) |
|---|---|---|---|
| 12.18 | 124.8 | 24.76 | 98.6 |
| 24.26 | 93.3 | 49.29 | 98.6 |
| 48.51 | 30.0 | 98.60 | 98.6 |
| 59.16 | 2.1 | 120.3 | 98.65 |

The gas-chromatographic analysis has shown no sensible variation in time of the concentration in acetic acid.

EXAMPLE 2

74.8 parts of gaseous ammonia are gradually added under agitation to 1000 parts of an aqueous solution containing 198 parts of formaldehyde, 11.5 parts of acetic acid, 1.5 parts of formic acid, 30 parts of trioxane and 1.5 parts of tetraoxane.

Operation is carried out at 35°–40° C, by means of external cooling with water, and at atmospheric pressure.

The progress of the reaction is followed by analysing samples of the solution taken at intervals of time.

The results of the analysis are reported in Table 2, wherein (A), (B), (C), (D) have the same meaning as in Table 1.

TABLE 2

| | | | |
|---|---|---|---|
| 18.7 | 148.8 | 38.30 | 99.4 |
| 38.0 | 97.9 | 77.94 | 99.5 |
| 54.6 | 54.2 | 112.0 | 99.5 |
| 74.8 | 0.7 | 153.6 | 99.65 |

The gas-chromatographic analysis has shown no sensible variation in time of the concentration in formic acid, acetic acid and trioxane.

EXAMPLE 3

With reference to the accompanying drawing, 1000 parts per hour of an aqueous solution containing 203 parts of formaldehyde, 8.9 parts of acetic acid, 1.0 parts of formic acid, 14.1 parts of methanol, 3.0 parts of methylal, 4.25 parts of methylformate and 8 parts of trioxane, are introduced through pipe 12 into a cylindrical reactor 10 carrying 10 sieve plates, between the seventh and the eighth plate.

Gaseous ammonia is delivered at a rate of 76.66 parts per hour through pipe 14 at the bottom of reactor 10.

Reactor 10 is operated at 55° C and at the pressure of 117 torr. The residence time under the reaction conditions is equal to 0.75 hours.

130.9 parts per hour of a gaseous mixture containing 103 parts of water, the remainder consisting of organic compounds, are removed at the top of column 10 through pipe 20.

This gaseous mixture is cooled and condensed in exchanger 22 and the liquid is collected in reservoir 23 connected through pipe 24 to a vacuum source.

A fraction of the solution discharged through pipe 16 from reactor 10 by means of pump 18 is recycled to the top of reactor 10 through pipe 17, whereas 945 parts per hour of discharged solution containing 156 parts of hexamine are delivered through pipe 26 to the static evaporator 28 of the falling film type.

Evaporator 28 is operated at a pressure of about 290 mmHg and with a residence time of the order of 10–20 seconds.

Besides, evaporator 28 is heated by condensation of the steam introduced into jacket 30 through pipe 32. The condensate is discharged through pipe 34.

566 parts per hour of vapours having a temperature of about 75° C are discharged through pipe 36. The vapours are cooled in exchanger 38 and the condensate is collected in reservoir 40 connected through pipe 42 to a vacuum source. 379 parts per hour of concentrated solution containing 156 parts of hexamine are tapped at the bottom of evaporator 28 and sent by means of pipe 44 and pump 46 to the thin film evaporator 48 equipped with a scraping device.

This evaporator is operated at atmospheric pressure, with a residence time of about 15 seconds, and heated by condensation of the steam introduced into jacket 50 through pipe 52. The condensate is discharged through pipe 54.

221.6 parts per hour of vapours are discharged at the top of evaporator 48 through pipe 56. These vapours are condensed in exchanger 58 and the condensate is collected in reservoir 60 connected through pipe 70 to a vacuum source. 157.4 parts per hour of solid hexamine are recovered through pipe 62 at the bottom of evaporator 48.

This hexamine has a titer of 99.1% and contains 0.8% of water and 0.05% of acetic acid.

This product is introduced into the horizontal drier 64, which is operated at 80° C and at a subatmospheric pressure. The drier 64 is connected to a vacuum source through pipe 66.

Analysis of the product discharged through pipe 68 shows the following results: titer in hexamine 99.8%; water content 0.18%; content in acetic acid lower than 0.02%.

What we claimed is:

1. A process for the recovery of formaldehyde from waste water containing the latter together with one or more lower saturated carboxylic acids which comprises:
   (1) reacting at a temperature of from 0° to 90° C said waste water with an amount of ammonia substantially equal to that stoichiometrically required to convert the formaldehyde present in said waste water into hexamine without substantial salification of said one or more lower saturated carboxylic acids, to thereby obtain an aqueous solution containing hexamine and said carboxylic acids, and
   (2) evaporating said aqueous solution at a temperature of from 20° to 120° C during a period of from 2 hours to 3 seconds to remove said water and said one or more lower saturated carboxylic acids in their acid form, thereby to recover said hexamine in solid form.

2. The process of claim 1, wherein said aqueous solution is evaporated by a two-step technique, comprising concentrating said solution in a first step to a hexamine content of from 25 wt.% to the saturation value and then evaporating said concentrated solution to obtain a solid hexamine having a water content lower than 1% by weight.

3. The process of claim 1, wherein said waste water contains at least 1% by weight of formaldehyde.

4. The process of claim 1, wherein said waste water contains from 5 to 25% by weight of formaldehyde.

5. The process of claim 1, wherein said waste water contains from 0.3 to 20% by weight of said one or more lower saturated carboxylic acids.

6. The process of claim 1, wherein said lower carboxylic acids are members of the group consisting of formic, acetic and propionic acids.

7. The process of claim 1, wherein said waste water, is reacted at a temperature of from 10° to 60° C and at a pressure equal to or lower than atmospheric.

8. The process of claim 1, wherein said aqueous solution is evaporated at a temperature of from 40° to 100° C, at a pressure equal to or lower than atmospheric and during a period of from one minute to 3 seconds.

9. The process of claim 1, wherein said aqueous solution is evaporated using the thin film or falling film technique and a static or dynamic evaporator.

10. The process of claim 1, wherein said aqueous solution is evaporated until solid hexamine is obtained with a water content lower than 1% by weight and a content one or more lower saturated carboxylic acids not exceeding 0.05% by weight.

11. The process of claim 1, wherein during said evaporation other impurities are also removed with said water and said one or more lower saturated carboxylic acids, such other impurities including derivative products of formaldehyde or hexamine.

12. The process of claim 1, wherein said aqueous solution is evaporated by a 2-step technique comprising:
   concentrating said solution in a first step to a hexamine content of from 25 weight percent to the saturation value; and subsequently
   evaporating said concentrated solution to obtain a solid hexamine having a water content lower than 1% by weight, wherein said evaporation is at a temperature of from 40° to 100° C and at a pressure equal to or lower than atmospheric during a period from 1 minute to 3 seconds.

13. The process of claim 12, wherein said aqueous solution contains, in addition to said formaldehyde and one or more lower saturated carboxylic acids an impurity selected from the group consisting of methanol, methylformate and methylal.

14. The process of claim 13, wherein said ammonia substantially completely converts said formaldehyde to hexamine instead of salifying the carboxylic acids present, whereby said acids can be distilled off together with water present along with said impurity.

15. The process of claim 14, wherein said recovered hexamine in solid form is free from coloured by-products of unpleasant smell.

* * * * *